United States Patent [19]

Blayo et al.

[11] Patent Number: 5,494,697
[45] Date of Patent: Feb. 27, 1996

[54] PROCESS FOR FABRICATING A DEVICE USING AN ELLIPSOMETRIC TECHNIQUE

[75] Inventors: Nadine Blayo, Jersey City; Dale E. Ibbotson, Bridgewater, both of N.J.; Tseng-Chung Lee, New York, N.Y.

[73] Assignee: AT&T Corp., Murray Hill, N.J.

[21] Appl. No.: 152,776

[22] Filed: Nov. 15, 1993

[51] Int. Cl.⁶ .................................................... H01L 21/66
[52] U.S. Cl. ................................ 427/10; 437/8; 437/225; 216/60
[58] Field of Search .......................... 427/10; 117/86; 118/688; 437/225, 8; 156/626

[56] References Cited

U.S. PATENT DOCUMENTS

| | | | |
|---|---|---|---|
| 4,637,123 | 1/1987 | Cazcarra et al. | 29/569 R |
| 4,874,240 | 10/1989 | Watts et al. | 356/73 |
| 5,087,591 | 2/1992 | Teng | 437/225 |
| 5,091,320 | 2/1992 | Aspnes et al. | 437/8 |
| 5,131,752 | 7/1992 | Yu et al. | 356/369 |
| 5,145,554 | 9/1992 | Seki et al. | 156/643 |
| 5,208,648 | 5/1993 | Batchelder | 356/237 |
| 5,220,403 | 6/1993 | Batchelder et al. | 356/345 |
| 5,223,914 | 6/1993 | Auda et al. | 356/381 |
| 5,270,222 | 12/1993 | Moslehi | 437/8 |
| 5,277,747 | 1/1994 | Aspnes | 156/626 |
| 5,354,575 | 10/1994 | Dagenais et al. | 427/10 |
| 5,362,356 | 11/1994 | Schoenborn | 156/626 |
| 5,395,769 | 3/1995 | Arienzo et al. | 437/7 |
| 5,403,433 | 4/1995 | Morrison et al. | 156/626 |

OTHER PUBLICATIONS

J. Vac. Sci. Technol. A 11(4), "In situ spectral ellipsometry for real-time thickness measurement: Etching multilayer stacks," by Steven A. Henck et al., (Jul./Aug. 1993) p. 1179.

J. Vac. Sci. Technol. B 10(6), "In situ ellipsometry and reflectometry during etching of patterned surfaces: Experiments and simulations," by M. Haverlag et al., (Nov./Dec. 1992) p. 2412.

Optical Materials 1, "Optical functions of silicon determined by two-channel polarization modulation ellipsometry," by G. E. Jellison, Jr., (1992) pp. 41–47.

J. Electrochem. Soc., Solid State Science and Technology, "Optical Etch-Rate Monitoring Using Active Device Areas: Lateral Interference Effects," by P. A. Heiman, vol. 132, No. 8, (Aug. 1985) p. 2003.

J. Electrochem. Soc.; Solid State Science and Technology, "Optical Etch-Rate Monitoring: Computer Simulation of Reflectance," by P. A. Heimann et al. (Apr. 1984) p. 881.

*Primary Examiner*—R. Bruce Breneman
*Assistant Examiner*—Matthew Whipple
*Attorney, Agent, or Firm*—Richard J. Botos

[57] ABSTRACT

An ellipsometric method for process control in the context of device fabrication is disclosed. An ellipsometric signal is used to provide information about the device during the fabrication process. The information is used to better control the process. An ellipsometric signal of a particular wavelength is selected. The signal is selected based on the composition and thickness of the films on the substrate through which the ellipsometric signal will pass before it is reflected from the substrate. Once the appropriate wavelength is determined, the ellipsometric signal is used to monitor the thickness of the films on the substrate over time, to assist in controlling the deposition and removal of films on the substrate, and to perform other process control functions in the context of device fabrication. The ellipsometric method is used to control the deposition and removal of films that underlie patterned masks with aspect ratios of 0.3 or more, that overlie topography on a substrate surface, or that both underlie a mask and overlie topography.

9 Claims, 4 Drawing Sheets

PROCESS FOR FABRICATING A DEVICE USING AN ELLIPSOMETRIC TECHNIQUE

BACKGROUND OF THE INVENTION

1. Technical Field

The invention is directed to a process for fabricating integrated circuit devices and in particular utilizing a measuring technique in conjunction with such processes.

2. Art Background

The move towards smaller design rules for the fabrication of integrated circuits is motivated by the desire to place a greater number of devices on a chip. For advanced device structures, both the film thickness of layers used to form these structures and the structure width must decrease as the number of devices on a chip increase. The presence of these smaller features, which are smaller in width and in thickness, has increased the complexity of fabricating integrated circuits. It is especially difficult to control the etching process (for example) of an integrated circuit when rapidly removing multiple layers of different materials from over a thin layer which must not be substantially affected. Typically, such processes require complex changes in processing conditions that must be made quickly.

An ellipsometer is frequently used to determine the characteristics of blanket films in the context of device fabrication. A beam of light is directed onto the surface of the film. The ellipsometer measures the light reflected from the film. From the reflected light the ellipsometer determines the angles DELTA ($\Delta$) and PSI ($\Psi$), which are defined as the change in phase of the light and the arc tangent of the factor by which the amplitude ratio of the incident and reflected light in the direction parallel to the plane of incident light changes, respectively. These quantities are then used to determine the optical characteristics such as the index of refraction, the film thickness, and the extinction coefficient of unpatterned, uniform films.

The use of an ellipsometer to derive $\Delta$ and $\Psi$ coordinates of a polarized light beam reflected from a work piece to monitor the thickness of a film deposited on a substrate is described in U.S. Pat. No. 5,131,752 to Yu et al. Yu et al. first calculate the endpoint, which is the point when a film of the desired thickness has been deposited, from the $\Delta$ and $\Psi$ values of a film of the desired thickness. Yu et al. calculate end point values of $\Delta$ and $\Psi$ from the known angle of incidence, the wavelength of the light source, the desired final film thickness, and the optical constants of the substrate and film at the process temperature. Therefore, the Yu et al. method is limited to controlling a process in which the precise endpoint is known.

In the context of device fabrication using masks or over topography, the precise endpoint of any process is difficult to determine due to the attendant irregularity of the surface. Masks as used herein are structures which are used to introduce a pattern onto or into a film or films overlying a substrate. Topography as used herein are surface irregularities or structures underlying films on a substrate. The optical path of an incident beam of light from an ellipsometer is affected by the presence of a mask or topography on a wafer, because the composition and/or configuration of the surface is irregular. Wafer, as used herein, is a substrate with films thereon. These irregularities cause the light reflected from the surface to be different than light reflected from uniform, blanket films. The mask or topography also affects the planarization state of light and therefore creates interference which adversely affects the quality of the signal that is reflected from the surface.

Henck, Steven A., et al., "In situ spectral ellipsometry for real-time thickness measurement: Etching multilyer stacks," *J. Vac. Sci. Technol. A.*, 11(4): 1179 (July/Aug. 1993) propose using an ellipsometer to monitor the film thickness in a large unpatterned region at the center of the wafer during plasma etching. The ellipsometer is first calibrated using known techniques. Then the ellipsometric parameters, $\Delta$ and $\Psi$, are determined from the thickness and the dielectric function of the film material. As the etch proceeds, the ellipsometer continues to transmit a beam of light toward the film and to measure the properties of the reflected light to obtain a useful signal. The changes in the reflected light indicate the decreasing thickness of the top layer of the film and the increasing proximity of the interface between the top layer and the layer underlying the top layer. Thus, during etching, an ellipsometer is used to determine how much of the top layer has been removed, which enables the etching to be terminated with a known film thickness remaining.

The technique described by Henck et al. requires an unpatterned topography-free area (or test pad) on the wafer in which to make the required measurements. An unpatterned, topography-free area on a device is undesirable, because it sacrifices that portion of the device real estate. Also, since an unpatterned, topography-free test pad requires different masking, etching, and deposition steps than patterned topography-containing areas, it can also complicate the lithographic process. Therefore, manufacturing costs will increase if a significant portion of the wafer has to be sacrificed to provide an area on which to perform the technique described by Henck et al.

Haverlag, M., et al., "In situ ellipsometry and reflectometry during etching of patterned surfaces: Experiments and simulations," *J. Vac. Sci. Technol. B*, 10(6):2412 (Nov./Dec. 1992) describe the use of ellipsometry at a single wavelength (632 nm) for the end point detection of a plasma etching process. Haverlag et al. conclude that such a technique cannot be used over typical patterned wafers because the end point was not detected when the incident ellipsometric light beam was aimed onto the surface in a direction that was perpendicular to the direction of lines formed by a mask over the film. Haverlag et al. observed that reflections of the light on the mask sidewalls inhibit the light from reaching the ellipsometric detector and concluded that an ellipsometric technique for plasma etch end point detection could only be used on patterned wafers with low, e.g., less than 0.3, aspect ratios.

However, in many applications for fabricating real devices, the aspect ratios of masks or topography are typically greater than 1.0. Also, as design rules decrease, more severe topography and higher aspect ratios are expected. Therefore, an ellipsometric technique for process control that can be used in processes for fabricating small design rule devices with topography over essentially all of the entire surface of the wafer is desired.

SUMMARY OF THE INVENTION

The process of the present invention uses an ellipsometric technique for process control during device fabrication. Specifically, the process is used to control those aspects of device fabrication that add materials to or remove materials from the substrate surface. In one example, the process is used to detect interfaces between two layers of a film on a substrate. Interface, as used herein, is the boundary between two layers of film, or between a layer of film and the substrate underlying the film. The process of the present invention provides information which is then used to control the device fabrication process either by changing the conditions under which a material is being deposited on or removed from a substrate, or by stopping the process altogether. The process provides this information by directing an ellipsometric light beam at the surface of the wafer being processed and monitoring the signal that is reflected.

The light signal so monitored for process control must be of a particular wavelength or range of wavelengths in order to provide the information necessary for process control when the wafer surface is irregular. Such surface irregularity occurs when a mask is deposited over the surface of the wafer being processed (a "patterned surface" herein) or there is an irregular surface ("topography" herein) underlying the film being processed. The appropriate wavelength is selected such that the absorption length is significantly smaller, e.g., a factor of 10, than the optical path through the film that is being ellipsometrically monitored. (The absorption length is defined as the depth in the material at which the incident electric field is decreased by 1/e relative to the incident field amplitude on the material.)

A way in which to select the initial wavelength is by performing the following calculation:

$$\frac{\lambda}{4\pi k_\lambda} \leq \frac{2n_\lambda d}{\cos \phi} \times \frac{1}{10}$$

wherein d is the initial nominal thickness of the layer being probed, $n_\lambda$ is the refractive index of the layer, $k_\lambda$ is the extinction coefficient of the film material at the wavelength $\lambda$ and $\phi$ is the angle of the incident beam relative to the normal from the surface of the wafer. The optical path is reduced by about a factor of 10 in the above calculation. However, appropriate wavelengths are obtained if the optical path is reduced by a factor of about 5 to about 20. Once the wavelength is selected, light of that wavelength is detected by the ellipsometer. The spectral refractive indices $n_\lambda$ and extinction coefficients $k_\lambda$ for various materials are obtained from sources for these coefficients such as Palik, D. E., et al., "Handbook of Optical Constants of Solids", Vol. 1 and 2 (1985).

Another means by which the appropriate wavelength is determined is by scanning a number of different wavelengths in a signal reflected from the substrate surface during a process in which the film thickness is being increased or reduced. The values of $\Delta$ and $\Psi$ over time, referred to as "ellipsometric traces", are observed. Those traces that exhibit an abrupt change in the slope of the values of $\Delta$ and/or $\Psi$ over time during the process are examined to determine if the abrupt change in slope indicates a transition in the process from one material to another. A trace that indicates the point during the process when the surface transitions from one layer of material to another is a useful tool for process control. Such an indication permits the process to be stopped at the appropriate time, or it permits process conditions to be changed in real time. The wavelength at which one such trace is obtained is used as the signal wavelength when performing the process on subsequent substrates with substantially identical films thereon.

Since ellipsometric traces are substantially identical for substantially identical processes on substantially identical wafers, these traces are used as tools for process control.

DETAILED DESCRIPTION

Figure 1:
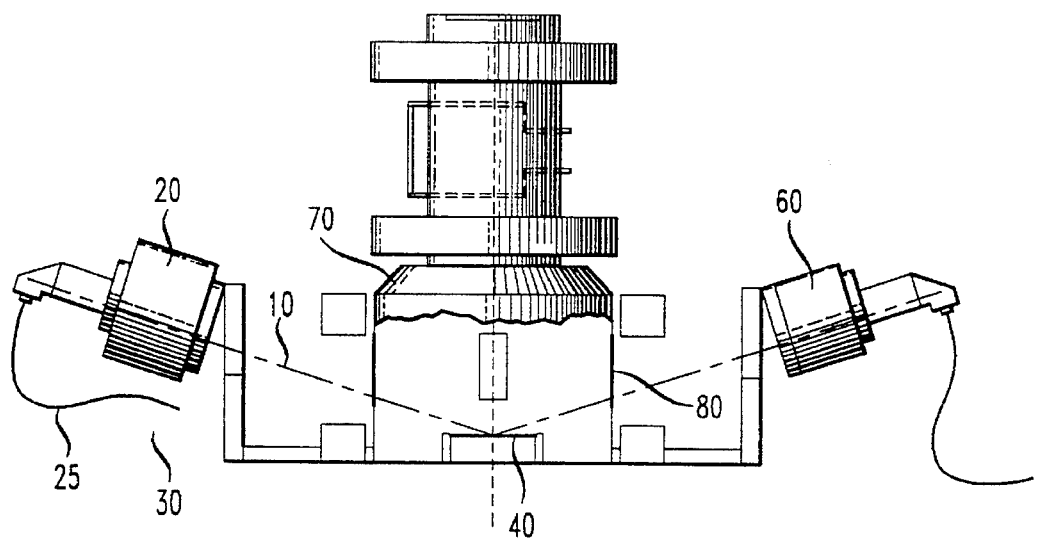
FIG. 1 is a schematic illustration of an ellipsometer as used in the present invention.

Illustrated in FIG. 1 is a simplified diagram of an ellipsometer as it is configured for use in the process of the present invention. It is contemplated that the process for controlling the removal of a film will be used in many different processes for thin film growth or etching of devices such as integrated circuits and other semiconductor and optical devices. However, the process of the present invention has been initially implemented in connection with the plasma etching of films upon a substrate and will be described in detail accordingly.

As shown in FIG. 1, a beam of incident light 10 is generated by the excitation head 20 of the ellipsometer 30. The light is generated from a light source (not shown) and transported to the head 20 via an optical fiber 25. The beam of light 10 is directed to strike a wafer 40. The excitation head 20 is positioned so that the angle of incidence 50 of the light beam 10 on the wafer 40 is about 70° from normal. Other angles of incidence are contemplated as useful depending upon the wafer. Angles of about 0° to about 90° are contemplated.

The incident light 10 is reflected from the wafer 40. The light signal so reflected is detected by the detection head 60 of the ellipsometer 30. The detection head 60 transmits the optical signal to a monochromator via a an optical fiber (not pictured). The monochromator is used to select the desired wavelength of light, which is then transmitted to a detector. The detector converts the optical signal to an electrical signal and then transmits that signal to a signal processor, which determines the $\Delta$ and $\Psi$ values for the reflected light.

The wafer 40 is placed in a chamber 70 in which the desired processing takes place. In FIG. 1, the chamber 70 depicted is suitable for plasma etching a film from the surface of the substrate. The chamber 70 is standard, except it is equipped with viewports 80 through which the ellipsometric signal enters and exits the chamber 70.

The process of the present invention, unlike previous processes, utilizes an ellipsometer for controlling the deposition and removal of films on substrates when there are patterned features with aspect ratios that are greater than 0.3 overlying the films, topography underlying the films or both patterned features over the film and topography under the film. The ellipsometer reports the values of $\Delta$ and $\Psi$ over time during a processing step in a device fabrication process. Since $\Delta$ and $\Psi$ are optical parameters of light reflected from the substrate, they are influenced by the optical path which the light must travel, i.e., through the layers on the substrate. As the thickness of these layers change, so do the values of $\Delta$ and $\Psi$. The values of $\Delta$ and $\Psi$ also change after a layer has been removed entirely from a portion of the wafer. An abrupt change in the slope of the trace of $\Delta$ and $\Psi$ over time during an etching step in a device fabrication process will indicate a change in the wafer surface, such as an interface between two materials.

However, if there is interference with the light reflected from the film, the changes in $\Delta$ and $\Psi$ caused by an interface or other significant change in surface composition or thickness are obscured. Such interference results from thickness variations, such as those between masked and unmasked zones on the portion of the surface intersected by the incident beam of light from the ellipsometer. If sufficiently obscured, a trace of $\Delta$ and $\Psi$ over time will not clearly indicate when an interface has been reached during the process. Such traces are not useful for the control of process parameters such as adjusting the process conditions, terminating the etching process, or changing the composition of the etchant when an interface between two layers has been reached.

The process of the present invention achieves the desired degree of control by selecting a particular wavelength of light that provides a trace which is used for process control in the above described manner. Once the appropriate wavelength is selected, the ellipsometer is used to obtain traces of values of $\Delta$ and $\Psi$ over time during the process. If the appropriate wavelength of light has been selected, the trace will indicate when during the process an interface between two films is reached even though there is a mask overlying the film and/or topography underlying the film.

Figure 2:
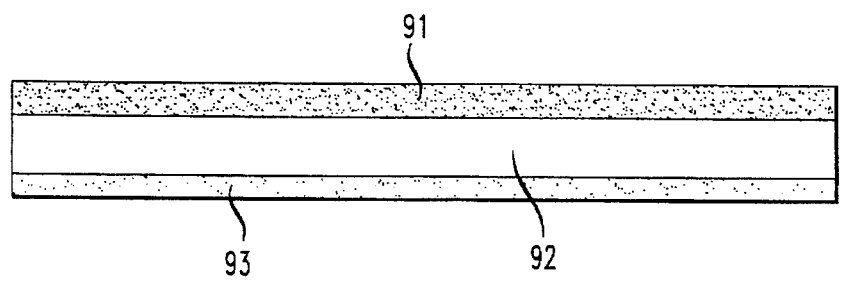
FIG. 2 is a side view of a blanket film of titanium nitride and polysilicon deposited over a thin silicon oxide layer.

The ellipsometric traces are referred to as signature traces, because they are substantially identical for a particular film etched under particular conditions. For example, if five wafers as illustrated in FIG. 2 were etched under substantially identical conditions, the traces obtained during the etch would be substantially identical as well. Thus, once a signature trace has been obtained for a particular wafer and process, the trace is used to control the processing of similar wafers in the same process. The traces also provide an indication that an interface is about to be reached during the process. This advance warning allows the process to be controlled with even greater accuracy.

In order to practice the process of the present invention, the wavelength of light used to generate the trace must be of a certain value. That wavelength is determined by considering a number of factors. Among these factors are: film thickness; the refractive index of the film material; the extinction coefficient of the film material at the relevant wavelength and the angle of incidence of the beam of light on the wafer surface.

If $\Delta$ and $\Psi$ are to be measured, the reflected light must be received by the detection head of the ellipsometer. Therefore, a wavelength must be selected such that the optical path through the layers is greater than the absorption length of the light in those layers. The choice of wavelength is therefore dependent on the composition and thickness of the film or films being investigated.

For example, a wavelength is selected by using the following formula:

$$\frac{\lambda}{4\pi k_\lambda} \ll \frac{2n_\lambda d}{\cos \phi} \quad (1)$$

wherein $n_\lambda$ is the refractive index of the film being probed, $k_\lambda$ is the extinction coefficient of the film material at the wavelength $\lambda$, and $\phi$ is the incident angle of the ellipsometric beam. The spectral refractive indices $n_\lambda$ and extinction coefficients $k_\lambda$ for the film materials are either obtained from reference data files or are determined experimentally using the ellipsometer to measure the spectrum of the blanket film. These values are also obtained in G. E. Jellison, Jr., "Optical Function of Silicon Determined by Two-channel Polarization Modulation Ellipsometry", *Optical Materials*, 1:46–47 (1992) and Palik, D. E., et al., "Handbook of Optical Constants of Solids", Vol. 1 and 2 (1985). If the film being monitored by the ellipsometer is a multilayer film, $n_\lambda$ and $k_\lambda$ are selected for the top layer material.

This formula provides a wavelength of light for which the absorption length through the particular film is much less than the optical path through the film. It is advantageous if the absorption length is a factor of about 5 to about 20 less than the optical path. It is particularly advantageous if the absorption length is at least a factor of 10 less than the optical path. For example, if the film on the substrate is a 2000 Å-thick (d) film of polysilicon, the following calculations are made to determine the appropriate wavelength:

| $\lambda$ (nm) | 375 | 428 | 632 |
|---|---|---|---|
| absorption length (nm)($\lambda/4\pi k_\lambda$) | 24 | 240 | 3200 |
| optical path (nm)/10 $\left[\frac{2n_\lambda d}{\cos\phi}\right]$ | 750 | 580 | 450 |

The above calculations illustrate that, for a 2000 Å-thick film of polysilicon, a wavelength that would provide a useful trace is 375 nm or 428 nm, because at both wavelengths, the absorption length is much less than the optical path. The 632 nm wavelength is not useful because the absorption length is longer than the optical path. It is contemplated that, for multilayer films, the wavelength at which the trace is generated will be varied during the process to accommodate each of the individual films being deposited or removed.

It is also possible to select the wavelength by obtaining traces of a film during a process at a number of different wavelengths. By observing the traces obtained, the trace that indicates the interface with the desired degree of clarity is selected. The wavelength used to obtain that trace is then used to monitor the processing of subsequent films. The wavelength of the light used to generate the trace is varied from process to process and from film composition to film composition because the wavelength selected depends upon the characteristics of the film and the process. Therefore, it is advantageous if the ellipsometer used in the process is equipped with a broad spectral light source and a mechanism on the detector for selecting the desired wavelength of light to generate the desired trace.

EXAMPLE 1

Use of the Process of the Present Invention to Control a Plasma Etch

The ellipsometer used to determine the ellipsometric parameters ($\Delta$, $\Psi$) was a UV-visible, phase modulated, spectroscopic ellipsometer made by the ISA division of Jobin-Yvon of Longjumeau, France. One skilled in the art will appreciate that other ellipsometers are equally suited to practice the process of the present invention. The ellipsometer was equipped with a white light source from a Xenon arc lamp. The light was polarized and passed through a phase modulator operating at 50 KHz. The excitation head of the ellipsometer was positioned such that the elliptically polarized light will hit a wafer at an angle of about 70° from normal. A detection head was mounted at −70° from normal. The wavelength of interest was observed by using a monochromator to exclude light of other wavelengths.

The ellipsometer was used to monitor the etching of films on several different wafers. One such film, depicted in FIG. 2, was a 1000 Å thick layer of titanium nitride 91 over a 2000 Å thick layer of polysilicon 92 over a 70 Å thick layer of an oxide of silicon 93. Another film, depicted in FIG. 3, was the same film as depicted in FIG. 2 but with a 2000 Å mask 94 of submicron features deposited thereover. A third film, as depicted in FIG. 4 is the film of FIG. 3, but deposited over a wafer with topography (not pictured) thereunder.

The wafers were placed in an etching tool that was manufactured by Lucas Labs of Sunnyvale, Calif. The tool was configured for single wafer processing of 125 mm diameter wafers. The wafer was clamped to a chuck. The temperature of the wafer was controlled using backside cooling with a helium purge by controlling the temperature of the chuck at about 0° C.

A low pressure, high density helicon plasma source, also made by Lucas Labs, was used to generate the plasma, which consisted of ions, electrons and reactive neutrals. The wafer was placed in the reaction chamber into which a gas was introduced. First, the native oxide was removed by igniting a plasma with 100 sccm of HBr and 20 sccm of $Cl_2$ at an rf-bias of 50 W for 10 seconds. The helicon source power was 2500 W and the reactor pressure was 2 mTorr.

The flow of the $Cl_2$ was shut off and the layer of titanium nitride was removed using the same conditions. Ten seconds after the titanium nitride was removed, the etchant recipe was changed by adding 20 sccm of a 20 percent/80 percent mixture of $O_2$ and helium to the 100 sccm of HBr to etch the polysilicon layer.

As the polysilicon layer was etched, the plasma recipe was again changed by reducing the rf-bias from 50 W to 25 W to avoid etching the thin oxide layer beneath the polysilicon. This change was made about 10 seconds after the $O_2$/helium was introduced.

Figure 3:
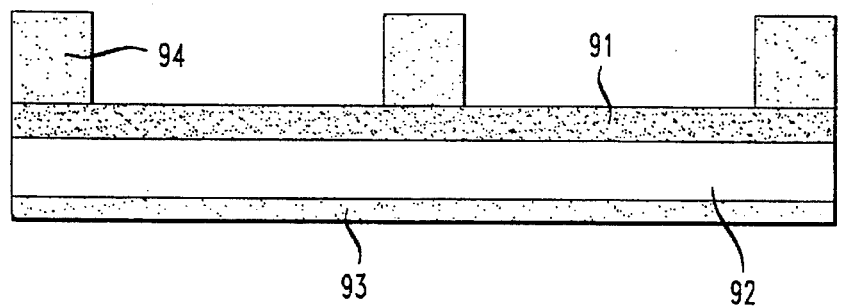
FIG. 3 is a side view of the blanket film of FIG. 2 with a mask thereover.
Figure 4:
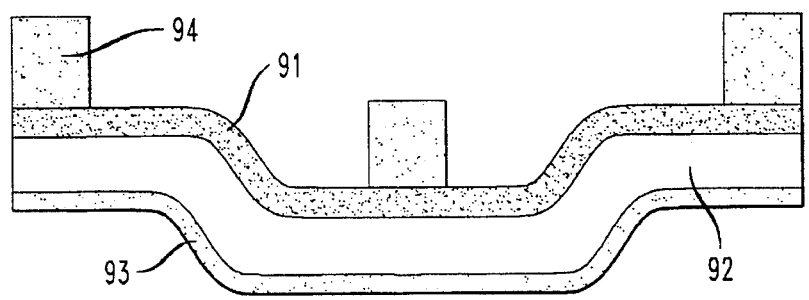
FIG. 4 is a side view of a film of titanium nitride and polysilicon deposited over topography with a mask thereover.

Ellipsometric traces were obtained while etching several wafers with the films described in FIGS. 2–4 deposited thereon. The ellipsometric traces were obtained using a monochromator to select various wavelengths to observe the effect of wavelength on the ellipsometric trace obtained.

Figure 5:
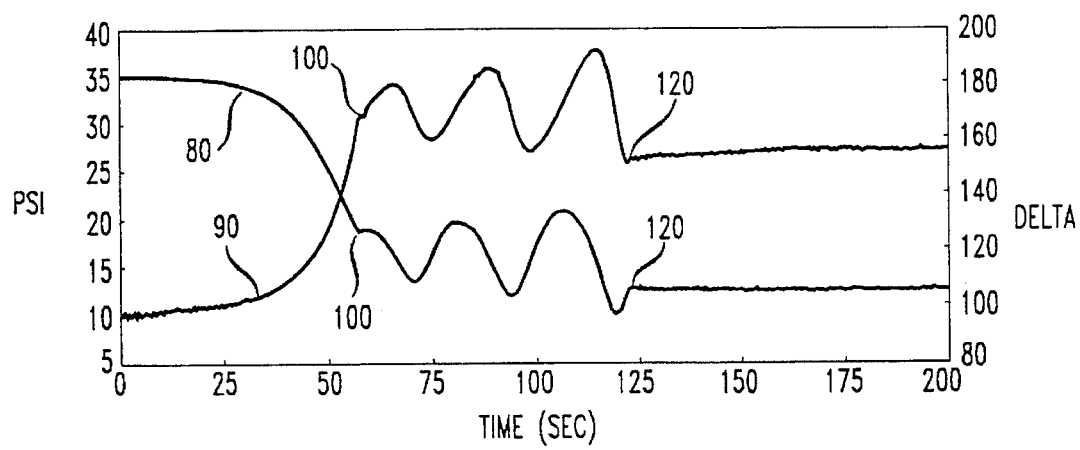
FIG. 5 illustrates the $\Delta$ and $\Psi$ traces recorded at 632 nm of the film depicted in FIG. 2 as it is being plasma etched.

A trace was obtained for a blanket film as illustrated in FIG. 2. This trace is illustrated in FIG. 5. The wavelength used to generate this trace was 632 nm. This wavelength is the wavelength used by single wavelength ellipsometers with a helium neon light source. The trace that was obtained indicates at what points in the process the first layer of titanium nitride and the second layer of polysilicon were removed. These points were indicated by abrupt changes in the slope of Δ80 and Ψ90 over time during the process. The point in the process when the titanium nitride was removed is indicated by point 100 and the point in the process when the polysilicon was removed is illustrated by point 120. Such traces are useful for process control during device fabrication because, by observing the trace, one can change the conditions to which the film is subjected. This is a great advantage in device fabrication, since many different materials are deposited on substrates and these materials react differently under different conditions. For example, some materials are very resistant to a particular etchant, while other materials may be removed rapidly by the same etchant. Therefore, the ability to either change conditions at a particular point in the process, such as when one layer has been removed, or to stop the process at a particular point, is extremely useful in the context of device fabrication.

Figure 6:
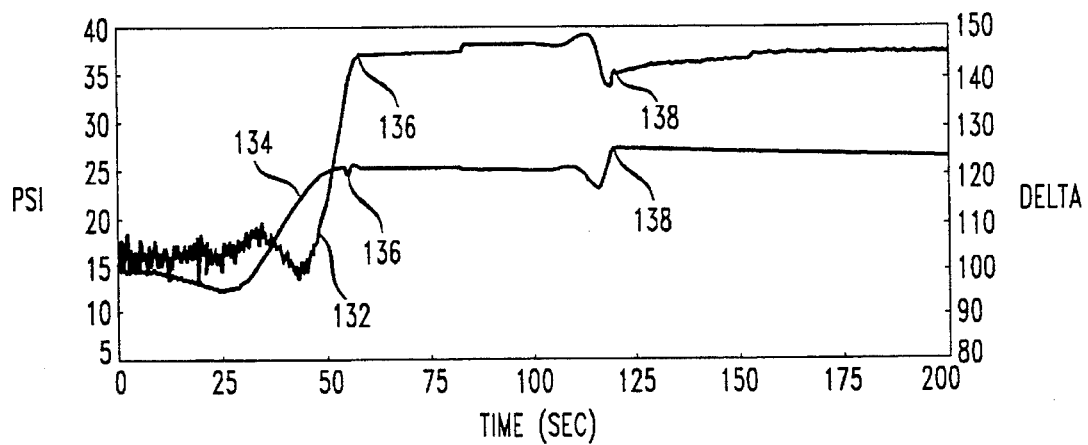
FIG. 6 illustrates the $\Delta$ and $\Psi$ traces recorded at 375 nm of the film depicted in FIG. 2 as it is being plasma etched.

FIG. 6 is another ellipsometric trace obtained while etching a film under the conditions described above. The film is again illustrated in FIG. 2. The wavelength of interest was selected by the process of the present invention. Again, the wavelength was obtained from the reflected light using a monochromator. The wavelength was 375 nm. Again, the traces clearly indicated the points during the process when the first layer of titanium nitride 136 and the second layer of polysilicon 138 were removed. Again, these changes were indicated by an abrupt change in the slope of Δ132 and Ψ134 over time during the process.

Figure 7:
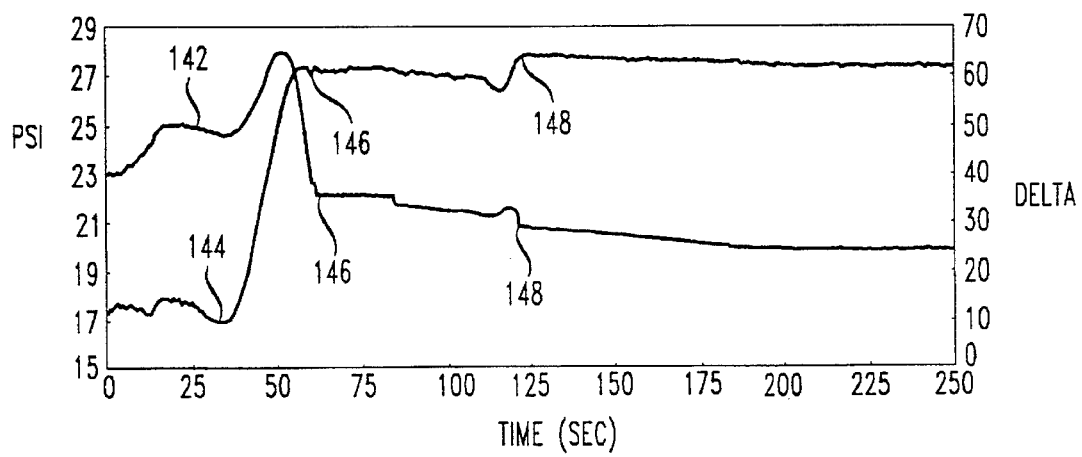
FIG. 7 illustrates the $\Delta$ and $\Psi$ traces recorded at 375 nm of the film depicted in FIG. 3 as it is being plasma etched.
Figure 8:
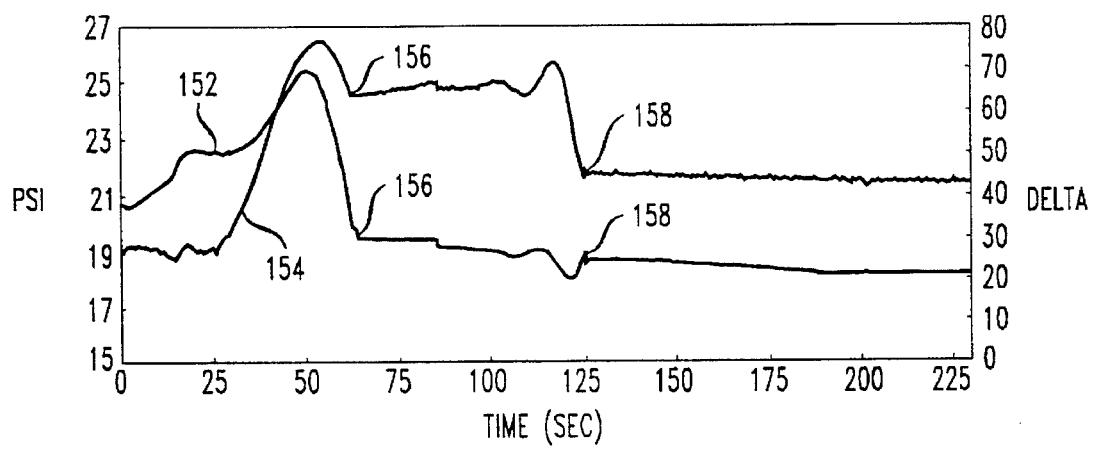
FIG. 8 illustrates the $\Delta$ and $\Psi$ traces recorded at 428 nm of the film depicted in FIG. 3 as it is being plasma etched.
Figure 9:
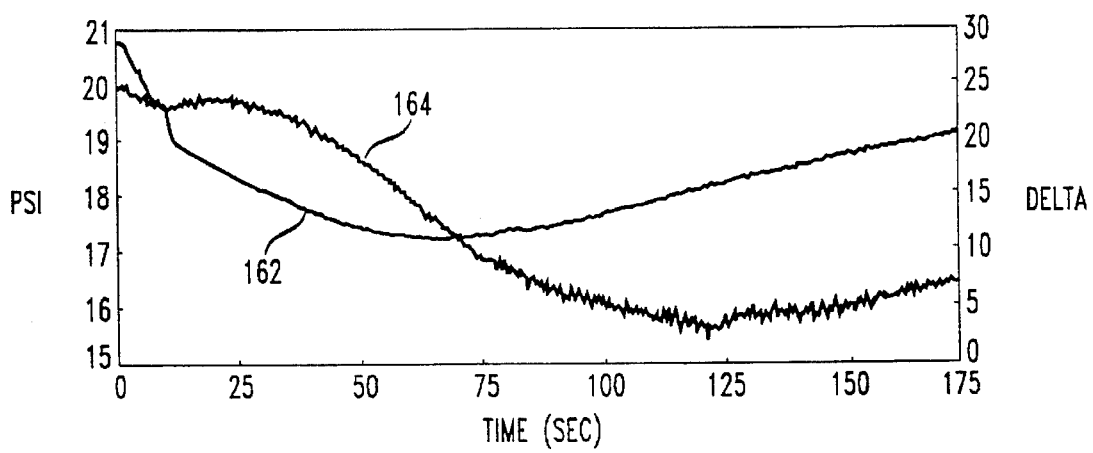
FIG. 9 illustrates the $\Delta$ and $\Psi$ traces recorded at 632 nm of the film depicted in FIG. 3 as it is being plasma etched.

FIGS. 7–9 are ellipsometric traces obtained while etching films described in FIG. 3 under the above-described conditions. In FIG. 7, the trace was obtained by first calculating the wavelength of interest to generate the trace using the method described above which was again 375 nm. The film had a silicon oxide mask thereover that was typical of masks used for integrated circuit fabrication.

The trace that was obtained clearly indicated the points during the process when the titanium nitride 146 and the polysilicon 148 were removed from the wafer. These points were again illustrated by the abrupt change in the slope of Δ142 and Ψ144 over time during the process.

FIG. 8 illustrates the effect that a change in the wavelength used to generate the trace will have on the trace that is obtained. The trace was obtained while etching a film as illustrated in FIG. 3 under the conditions described above. The conditions were identical to the conditions under which the trace depicted in FIG. 7 was obtained. The only difference was that the wavelength used to generate the trace was 428 nm.

FIG. 8 clearly indicates the points during the process when the titanium nitride 156 and the polysilicon 158 were removed. These points were again illustrated by abrupt changes in the slope of Δ152 and Ψ154 over time during the process. FIGS. 7 and 8 illustrate that a range of appropriate wavelengths are provided by the above formula 1. This formula provides a mechanism to select a wavelength in the appropriate range. This wavelength is then increased or decreased, depending upon the requirements of a particular process. Once the appropriate wavelength is approximated, one skilled in the art will appreciate how much the wavelength will be increased or decreased in order to obtain specific processing objectives.

FIG. 9 illustrates that, when processing films with a mask thereover, not every wavelength of light will provide a useful trace. The trace in FIG. 9 was obtained while etching a film as illustrated in FIG. 3 under the conditions described above. The mask 94 had an aspect ratio of 0.4 (2000 Å high/5000 Å wide). The wavelength of light used to generate the trace was 632 nm, a wavelength that is typically selected for performing ellipsometry. The trace obtained does not indicate at what points during the etch that the titanium nitride and polysilicon were removed because there is no point during the etch when the slope of Δ162 and Ψ164 changed abruptly over time.

The trace illustrated in FIG. 5 was also obtained at this wavelength. However, the trace in FIG. 5 does indicate when the interfaces were encountered during the process. This is due to the fact that the trace in FIG. 5 was obtained when etching a blanket film. Blanket films do not generate the same type of ellipsometric signals, nor do they provide the same degree of interference with these signals as do high aspect ratio masks and topography. Therefore, although a useful trace is obtained at a particular wavelength for a blanket film, that wavelength will not necessarily provide a useful trace for fabrication process control for patterned wafers. FIG. 9, therefore illustrates that the appropriate wavelength must be selected to obtain an ellipsometric trace that is useful for controlling a lithographic process when a mask is deposited on the wafer.

Figure 10:
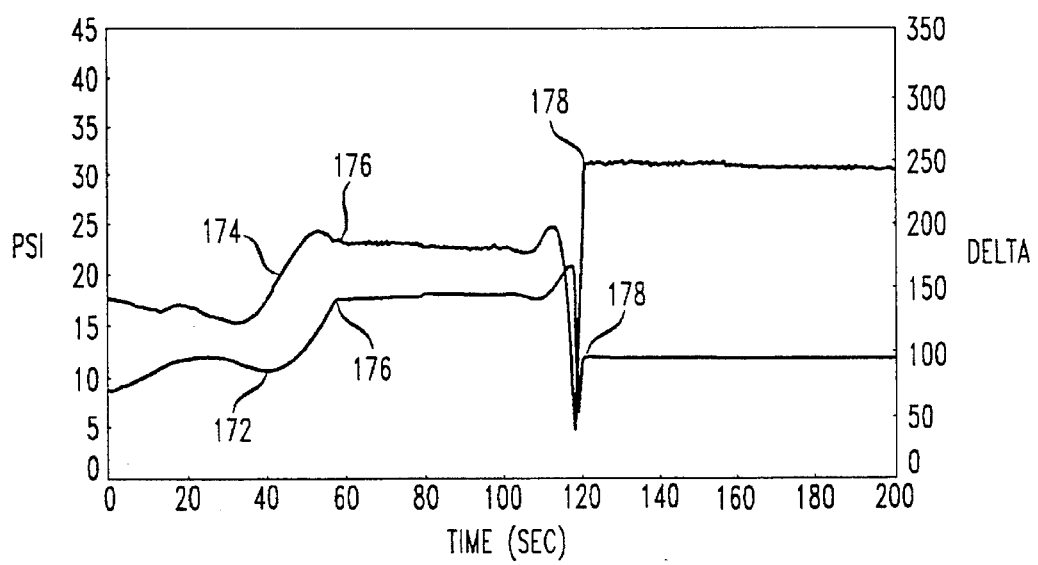
FIG. 10 illustrates the $\Delta$ and $\Psi$ traces recorded at 375 nm of the film depicted in FIG. 4 as it is being plasma etched.

A trace was obtained by etching a film as illustrated in FIG. 4 under the conditions described above. The wavelength of light used to generate the trace was 375 nm and was calculated as described above. The trace that was obtained is illustrated in FIG. 10. The trace clearly illustrates the points in the process when the titanium nitride 176 and the polysilicon 178 are removed from the wafer. These points are again indicated by an abrupt change in the slope of $\Delta$172 and $\Psi$174 over time.

Figure 11:
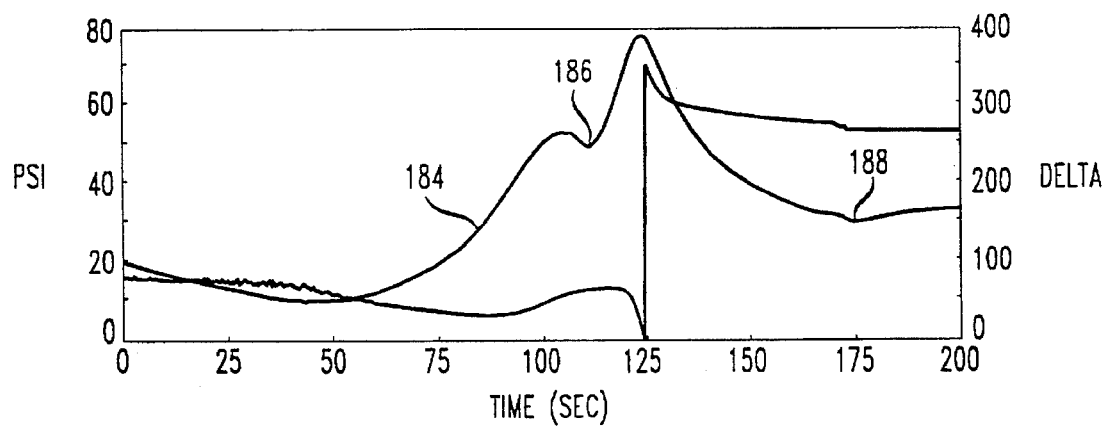
FIG. 11 illustrates the $\Delta$ and $\Psi$ traces recorded at 375 nm of the film depicted in FIG. 3 during plasma etching, wherein the ellipsometer beam is directed parallel to the lines in the mask.
Figure 12:
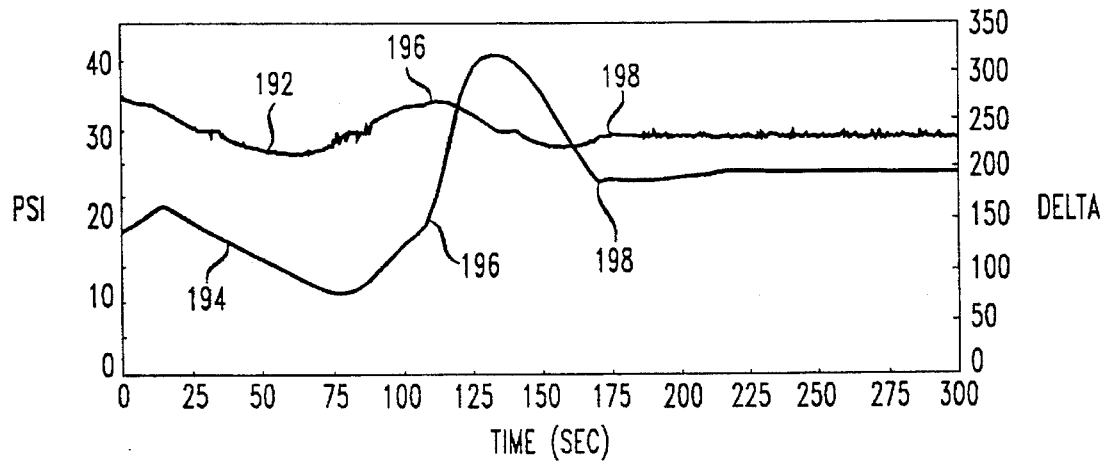
FIG. 12 illustrates the $\Delta$ and $\Psi$ recorded at 375 nm of the film depicted in FIG. 3 during plasma etching, wherein the direction of the ellipsometer beam is perpendicular to the direction of the lines in the mask.

The process of the present invention is useful even if there is a mask or topography over the entire wafer surface. As mentioned previously, prior art ellipsometric processes required a large area with no mask and no topography in order to practice the ellipsometric technique. As illustrated by FIGS. 11 and 12, useful traces are obtained even if the mask is a series of submicron lines and spaces over the entire substrate surface. The lines in the mask used to obtain the trace depicted in FIG. 11 had an aspect ratio of about 1. The trace in FIG. 11 was obtained by etching a film as depicted generally in FIG. 3, wherein the mask was a series of submicron lines and spaces. The incident beam was in a direction that was parallel to the direction of the lines and spaces on the mask. The wavelength used to generate the trace was 375 nm and was calculated as described above. The trace obtained indicates the points during the etch when the titanium nitride 186 and the polysilicon 188 layers were removed from the wafer. However, this indication was provided only by the change in the rate at which the value of $\Psi$184 changed during the process. Therefore, the change in one of either optical parameter, $\Delta$ or $\Psi$, will provide the information necessary for device fabrication process control.

FIG. 12 was obtained under the identical conditions used to obtain the trace illustrated in FIG. 11, except that the direction of the incident beam of light was perpendicular to the direction of the lines and spaces on the mask overlying the film. FIG. 12 illustrates that the trace obtained under these conditions does indicate the points during the etch when the titanium nitride 196 and the polysilicon 198 were removed. In this trace, the point in the process at which the titanium nitride was removed was indicated by the peak value of $\Delta$192 and the point at which the polysilicon was removed was indicated by the abrupt change in the slope of $\Psi$194.

As mentioned previously, once a signature trace is obtained for a particular film under particular conditions, that trace is used to control the processing of substantially identical films under substantially identical conditions. If the appropriate wavelength is selected, the point in the process between films will be indicated by a marked change in the value or slope of at least one of the ellipsometric angles $\Delta$ and $\Psi$. The particular type of change will vary widely from trace to trace, however.

It is contemplated that the process of the present invention will be used to observe and control numerous aspects of device fabrication that require deposition or removal of materials over irregular surfaces. For example, the process is used to control the deposition of films onto substrates in addition to controlling the removal of those films as described above. After the appropriate wavelength is selected, the process is used to control deposition much in the manner of the processes described in U.S. Pat. No. 5,091,320 to Aspnes et al. and U.S. Pat. No. 5,131,752 to Yu et al., both of which are incorporated by reference. It is contemplated that the film will be grown under the dry deposition conditions described in Aspnes et al.

For example, once a signature trace is obtained, the deposition of a multilayer film over topography or other surface irregularity is monitored and controlled by observing the trace being obtained in real time during the deposition process. The trace indicates the thickness of the first layer because the slope of $\Delta$ and/or $\Psi$ is relatively constant over a period of time. When that period of time has elapsed, the desired thickness has been deposited.

The process conditions are then changed to begin depositing the second layer of film. The point in time when deposition of the second film begins is characterized by an abrupt change in the slope of $\Delta$ and/or $\Psi$. This indicates the point during the process when the deposition begins for the second layer of film. By indicating the starting point, the deposition of the second layer is controlled, because one can identify the point in time during the process when deposition of this layer commenced. From this information one can determine when the desired amount of material has been deposited by simply observing the length of time that elapses from the point during the process when deposition began. This observation cannot be made using a trace such as the one illustrated in FIG. 9, because no interface is indicated by the trace.

We claim:

1. A process for fabricating a device comprising:

positioning a substrate with an irregular surface in a chamber;

providing an ellipsometric signal by generating the signal and aiming the signal at the substrate;

determining a wavelength of light for the ellipsometric signal such that the absorption length of the light is a factor of about 5 to about 20 less than the length of the optical path of the light through a film on the substrate;

observing an ellipsometric signal of the determined wavelength;

using the determined wavelength to generate an ellipsometric trace;

subjecting the substrate to conditions which change the thickness of the film on the substrate;

observing the trace as the thickness of the film changes; and controlling the conditions which change the thickness of the film on the substrate based on the generated trace.

2. The process of claim 1 wherein the irregular substrate surface has topography underlying the film on the substrate.

3. The process of claim 1 wherein the wavelength of the signal is selected by calculating:

$$\frac{\lambda}{4\pi k_\lambda} \leq \frac{2 n_\lambda d}{\cos \phi} \times \frac{1}{10}$$

wherein d is the thickness of the film, $n_\lambda$ is the refractive index of the film, $k_\lambda$ is the extinction coefficient of the film at the wavelength $\lambda$, and $\phi$ is the angle of the incident beam relative to the normal from the substrate surface.

4. The process of claim 1 wherein the wavelength of the signal is determined by generating multiple ellipsometric traces using multiple ellipsometric signals each at a different wavelength and, by observing the changes in $\Delta$ and $\Psi$ as the thickness of the film changes for each of the traces, selecting the wavelength for the ellipsometric signal.

5. The process of claim 1 wherein the irregular substrate surface is a substrate with a layer of film over which is placed a patterned mask and the conditions which change the thickness of the film are plasma etch conditions.

6. The process of claim 5 wherein the patterned mask over the layer of film has an aspect ratio that is greater than 0.3.

7. The process of claim 1 wherein the conditions which change the thickness of the film are plasma etch conditions.

8. The process of claim 1 wherein there are surface irregularities on that portion of the substrate on which the ellipsometric signal is incident.

9. The process of claim 1 wherein the conditions which change the thickness of the film are conditions which grow the film by deposition.

* * * * *